(12) United States Patent
Mannhardt et al.

(10) Patent No.: US 8,379,192 B2
(45) Date of Patent: Feb. 19, 2013

(54) APPARATUS FOR OPTICAL MEASUREMENT OF SUBSTANCE CONCENTRATIONS

(75) Inventors: Joachim Mannhardt, Eschach (DE); Trevor Page, Southampton (GB)

(73) Assignees: J&M Analytik AG, Essingen (DE); GEA Process Engineering (NPS) Ltd, Eastleigh, Hampshire (GB)

( * ) Notice: Subject to any disclaimer, the term of this patent is extended or adjusted under 35 U.S.C. 154(b) by 576 days.

(21) Appl. No.: 12/161,113

(22) PCT Filed: Feb. 1, 2007

(86) PCT No.: PCT/EP2007/000838
§ 371 (c)(1),
(2), (4) Date: Mar. 29, 2010

(87) PCT Pub. No.: WO2007/088047
PCT Pub. Date: Aug. 9, 2007

(65) Prior Publication Data
US 2010/0214556 A1 Aug. 26, 2010

(30) Foreign Application Priority Data

Feb. 1, 2006 (DE) .......................... 10 2006 004 916

(51) Int. Cl.
*G01N 21/00* (2006.01)
(52) U.S. Cl. ......................................................... 356/73
(58) Field of Classification Search ..................... 356/73, 356/244, 432; 250/458.1
See application file for complete search history.

(56) References Cited

U.S. PATENT DOCUMENTS

| | | | |
|---|---|---|---|
| 3,141,094 A | 7/1964 | Strickler | |
| 4,596,468 A * | 6/1986 | Simeth | 356/400 |
| 4,786,171 A | 11/1988 | LeFebre et al. | |
| 5,011,587 A | 4/1991 | Schmidt | |
| 5,335,067 A | 8/1994 | Prather et al. | |
| 5,708,273 A | 1/1998 | VonBargen | |
| 5,724,151 A * | 3/1998 | Ryley et al. | 356/432 |
| 7,113,265 B1 * | 9/2006 | Sarrazin et al. | 356/73 |

FOREIGN PATENT DOCUMENTS

| | | |
|---|---|---|
| DE | 1959612 A1 | 6/1971 |
| DE | 3339950 A1 | 5/1985 |
| DE | 37243593 A1 | 2/1988 |
| DE | 3820405 C2 | 8/1989 |
| DE | 93 19 750.0 U1 | 2/1994 |
| DE | 19843553 A1 | 4/2000 |
| EP | 0144929 A2 | 6/1985 |
| EP | 0415877 A2 | 6/1985 |
| EP | 0391836 B1 | 10/1990 |
| EP | 1321756 A1 | 6/2003 |
| JP | 62025239 A | 2/1987 |
| JP | 08029345 | 2/1996 |

* cited by examiner

*Primary Examiner* — Tarifur Chowdhury
*Assistant Examiner* — Abdullahi Nur
(74) *Attorney, Agent, or Firm* — GrayRobinson, P.A.

(57) ABSTRACT

An apparatus for optical measurement of substance concentrations has at least one transmitter arranged in or on a housing and at least one receiver for optical radiation, and a deflection device, which is at a distance from the at least one transmitter and the at least one receiver and is arranged within the substance when the apparatus is being used correctly, for deflection of the optical radiation from the at least one transmitter to the at least one receiver. The distance between the deflection device and the at least one transmitter and/or the at least one receiver can be varied by means of an adjusting device.

18 Claims, 5 Drawing Sheets

APPARATUS FOR OPTICAL MEASUREMENT OF SUBSTANCE CONCENTRATIONS

CROSS REFERENCE TO RELATED APPLICATIONS

This application claims priority under 35 U.S.C. Sections 119 (a)-(d), 120, 363 and 365 to PCT/EP2007/000838, filed Feb. 1, 2007 which designated the United States and at least one other country in addition to the United States and claimed priority to German Application No. 10 2006 004 916.0 filed Feb. 1, 2006. The specifications of these applications are expressly incorporated by reference into this application in their entirety.

BACKGROUND OF THE INVENTION

The invention relates to an apparatus for the optical measurement of substance concentrations, having a transmitter and a receiver for optical radiation of the type defined in more detail in the preamble of claim 1.

A generic apparatus is known, for example, from DE 93 19 750 U1. Such apparatuses, generally also referred to as immersion probes, are usually used to analyze liquids for example in chemical, biological and pharmaceutical research, production and inspection. However, they are also used in bulkable substances, such as powders or granules. Here, optical radiation, usually light, is used to measure the absorption effected by the medium when it is permeated by the optical radiation.

In practice, a frequent problem with such apparatuses is that it is necessary in some applications to measure varying layer thicknesses of the substance. To this end the measurement probe and/or the deflection device for the optical radiation need to be replaced in the known apparatuses, which results in disruptions to the operation which are sometimes significant.

It is therefore an object of the present invention to provide an apparatus for the optical measurement of substance concentrations which can be used to measure varying layer thicknesses of substances to be examined with relatively little complexity.

This object is achieved according to the invention by way of the features mentioned in claim 1.

The adjustment device according to the invention makes it possible to change the distance between the deflection device and the transmitter and/or the receiver in a way such that the layer thickness of the substance to be measured can also be varied during the measurement. Advantageously, as a result, no more disruptions to the operation are necessary, which leads to a significant saving in terms of time and thus costs.

This variability of the layer thickness of the substance to be measured makes it possible in addition for the sensitivity of the apparatus to be matched very easily to the respective measurement task. It is another advantage of the adjustment device according to the invention that the deflection device can in this way be moved to a different location, for example in order to be cleaned.

A very simple and practicable embodiment of the invention can provide for the adjustment device to have at least one holding element and a displacement element which is mounted in the at least one holding element such that it can be displaced, with one of the components of the adjustment device being connected to the housing and the other component being connected to the deflection device.

An embodiment of the adjustment device in which the latter can be adjusted manually is particularly simple and thus cost-effective.

In order to make the operation of the adjustment device more convenient, it can, however, also be provided that the latter can be adjusted by electrical, hydraulic or pneumatic means.

In another very advantageous embodiment of the invention, the deflection device can be adjusted with respect to the transmitter and the receiver in a manner such that the deflection device forms a closed hollow space with the housing.

This closed hollow space makes it possible to carry out reference measurements on substances introduced into the hollow space without removing the apparatus from the substance, which can likewise contribute to the simplification of the process.

If in this connection a flushing device for flushing the hollow space between the housing and the deflection device is provided, simple flushing of the hollow space and thus cleaning of the surfaces surrounding the hollow space is possible, likewise without having to remove the apparatus from the substance. In this case it is furthermore possible to introduce reference media into the hollow space.

Other advantageous refinements and developments of the invention emerge from the remaining dependent claims. Exemplary embodiments of the invention will be illustrated in terms of their principle below with reference to the drawing, in which:

DETAILED DESCRIPTION OF THE PREFERRED EMBODIMENT

Figure 1:
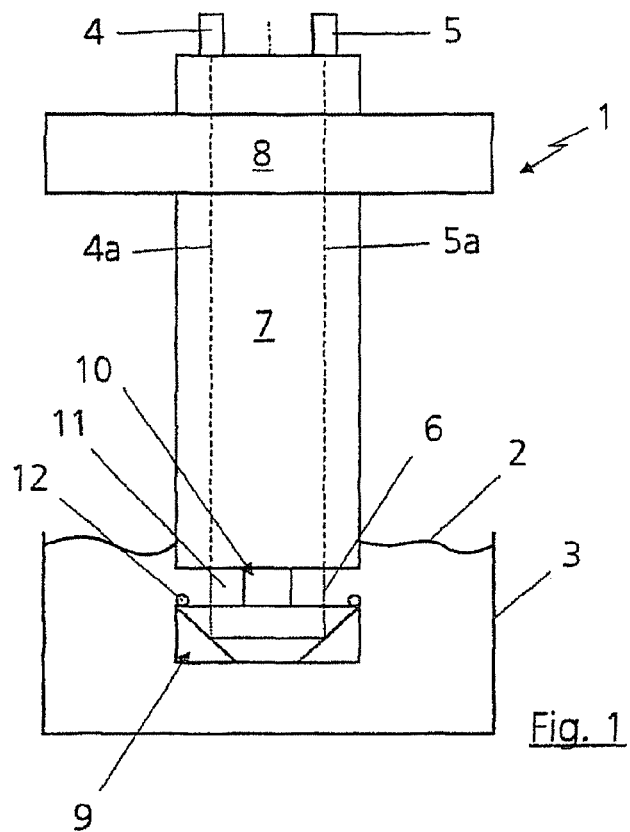
FIG. 1 shows a first embodiment of the apparatus according to the invention for the optical measurement of substance concentrations.

FIG. 1 shows an apparatus 1 for measuring the concentration of a substance 2 which is held in the present case in a container 3. The substance 2 can be a liquid, if appropriate containing a dissolved additive, or a bulk material, such as powders, grains or granules. The apparatus 1 can also be referred to as an immersion probe and has a transmitter 4 and a receiver 5 for optical radiation 6. The optical radiation is preferably light, and the transmitter 4 and the receiver 5 have optical waveguides 4*a* and 5*a* which are respectively associated with the former.

A housing 7, having a flange 8 by means of which it can be fastened to existing measuring apparatuses or the like, accommodates the transmitter 4 and the receiver 5. The apparatus 1 furthermore has a deflection device 9 which is arranged, if the apparatus is used correctly, in the substance 2 and serves for the deflection of the optical radiation 6 emitted by the transmitter 4 towards the receiver 5. The deflection device 9, which is not illustrated in more detail until FIGS. 4 and 5, can be adjusted with respect to the housing 7 and thus with respect to the transmitter 4 and the receiver 5 using an adjustment device 10. In this manner, varying layer thicknesses of the substance 2 can be measured using the apparatus 1 without removing the latter from the substance 2. Moreover, the adjustment device 10 makes it possible to move the deflection device 9 through a seal (not illustrated) in the flange 8 in order to clean the same outside the process, for example. If in so doing the deflection device 9 is moved completely up to the housing 7, the result is a smooth, continuous surface without an interrupting edge, so that the seal is not damaged.

In order to create a hollow space 11 between the housing 7 and the deflection device 9, which space can enclose a certain amount of the substance 2, the deflection device 9 can be moved so close to the housing 7 that the hollow space 11 which is closed off from the outside is formed. To this end, the apparatus 1 has a seal 12 which is attached in the present case to the deflection device 9 and ensures that the hollow space 11 which is created in said manner is sealed well.

Figure 2:
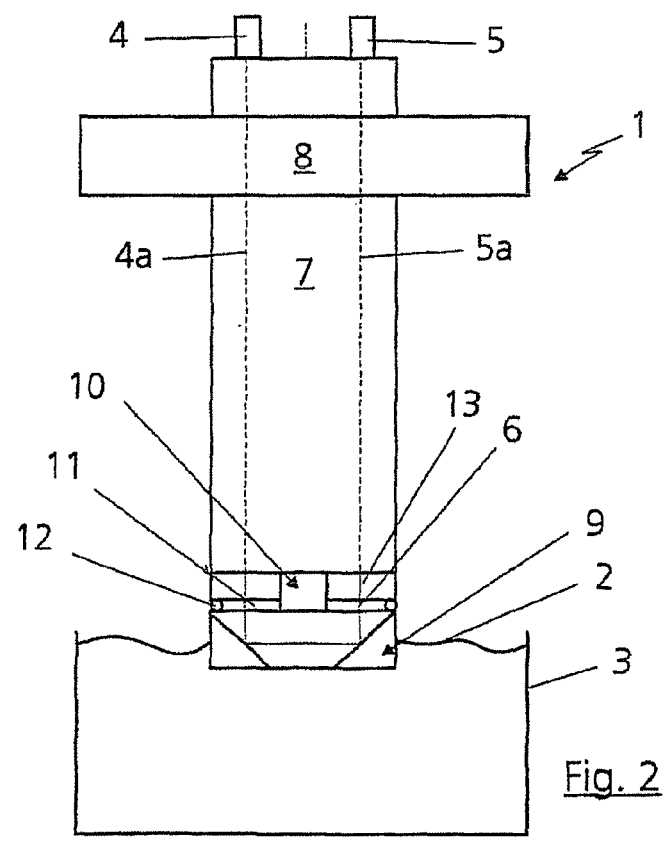
FIG. 2 shows a second embodiment of the apparatus according to the invention for the optical measurement of substance concentrations.

The embodiment of the apparatus 1 illustrated in FIG. 2 has a collar 13 on the underside of the housing 7, that is to say on that side of the housing which faces the deflection device 9, which collar 13 reduces the distance between the deflection device 9 and the housing 7 and provides a minimum distance between them. It is possible in this manner to additionally influence the layer thickness of the substance 2 which can be measured using the apparatus 1. The seal 12 sealing off the hollow space 11 from the outside is also provided here. In principle, the seal 12 can also be attached further inside when viewed in the radial direction. In all embodiments of the apparatus 1, a distance measuring device (not illustrated) for measuring the distance between the deflection device 9 and the transmitter 4 and the receiver 5 or the housing 7 can additionally be provided.

Figure 3:
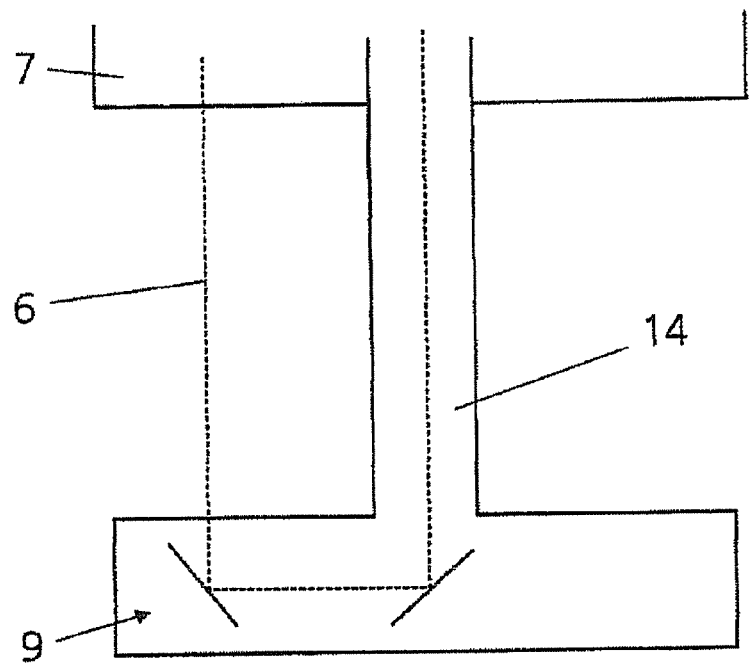
FIG. 3 shows, in the corresponding subfigures, parts of other embodiments of the apparatus according to the invention for the optical measurement of substance concentrations.

Whereas the deflection device 9 in FIGS. 1 and 2 is configured such that the optical radiation 6 passes twice through the substance 2, i.e. on the way from the housing 7 to the deflection device 9 and on the way back from the deflection device 9 to the housing 7, the deflection device shown in FIG. 3 is arranged such that the optical radiation 6 passes but once through the substance 2. For this purpose, a pipe 14, through which the optical radiation 6 is guided, is arranged in the region between the housing 7 and the deflection device 9. In the present case, the optical radiation 6 is guided in the pipe 14 on the way from the deflection device 9 into the housing 7, but the optical radiation 6 could likewise be guided in the pipe 14 on the way from the housing 7 to the deflection device 9. The arrangement shown in FIG. 3 is used when the substance 2 to be examined exhibits very high absorption such that, if the optical radiation 6 were to pass through it twice, said radiation would lose too much energy.

Figure 3A:
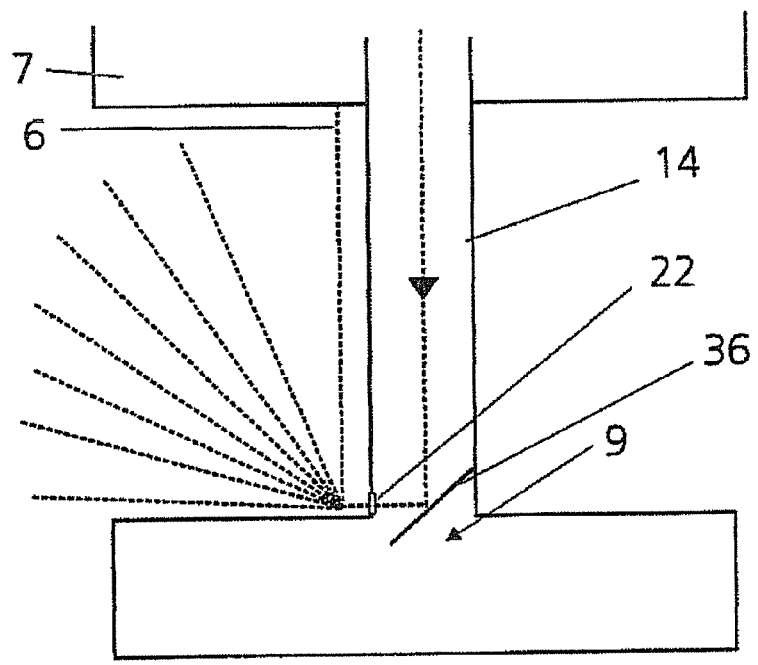

FIG. 3a shows another variant of the invention which is suitable in particular for carrying out fluorescence measurements. The distinctive characteristic of the variant illustrated in this figure is that the optical radiation used in the measurement is directed in a manner such that the incident optical radiation and the optical radiation which is deflected, or scattered, or emitted by the substance to be measured are aligned at an angle of approximately 90° with respect to one another. This is achieved in the embodiment illustrated in FIG. 3a by virtue of the fact that the deflection device 9, which in the present case shows a simple mirror 36, is configured such that the optical radiation is directed, via the mirror 36, through the optical window 22 at right angles to the pipe 14 and into the substance to be measured. As FIG. 3a indicates, the optical radiation is deflected by the substance to be measured in a wide variety of directions; only that component of the optical radiation which is deflected at right angles to the direction of incidence, however, reaches the receiver 5 (not illustrated) arranged in the housing 7. Thus the geometry of the arrangement enables fluorescence measurements to be carried out.

Figure 3B:
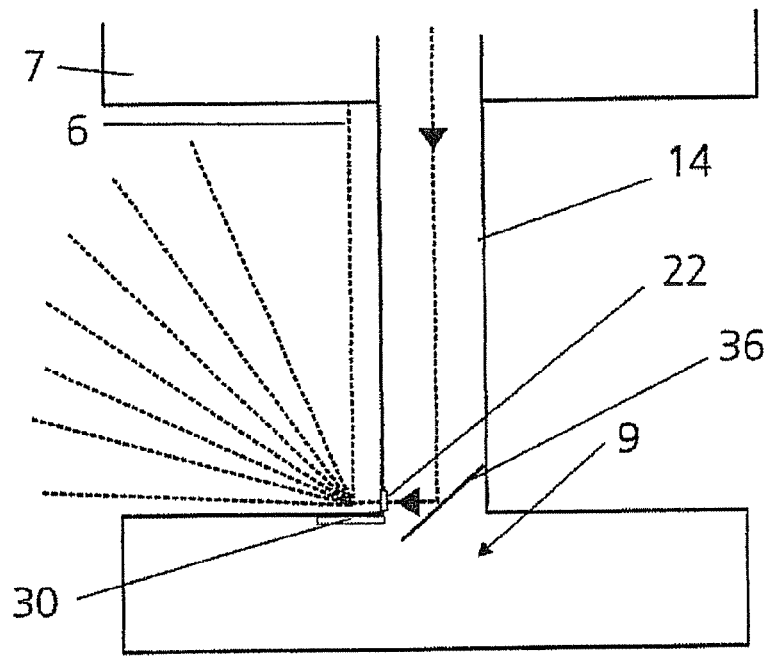

Subfigure 3b illustrates a variant of the apparatus shown in FIG. 3a. FIG. 3b shows the further mirror 30 as an additional component, which mirror 30 is used to reflect even that component of the optical radiation 6 in the direction of the receiver 5 which is emitted by the substance to be measured in the direction opposite the receiver 5. The efficiency of the fluorescence measurement described in FIG. 3a is thus increased further.

Figure 3C:
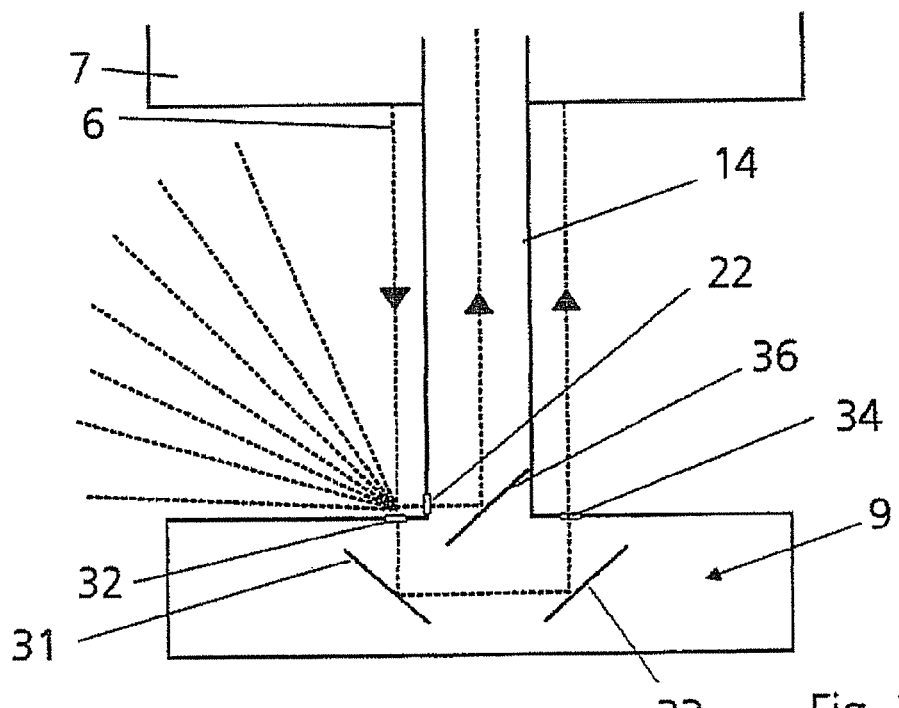

FIG. 3c shows another embodiment of the invention which allows the parallel or else sequential measurement of absorption, scattering and fluorescence.

As compared to FIG. 3b, in the case shown in FIG. 3c the direction of the optical radiation 6—as indicated by the arrows—is opposite. The transmitted component, or the component which is scattered in the forward direction, of the optical radiation 6 passes through the first optical window 32 and strikes the mirrors 31 and 32, where they are deflected in the direction of the receiver 5 (not illustrated) and pass through the second optical window 34. The component of the optical radiation 6 which is deflected or emitted in the perpendicular direction by the substance to be measured passes through the optical window 22 in the direction of the pipe 14 and is deflected, in the pipe 14, in the direction of the receiver 5 (not illustrated) by the mirror 36.

Rather than the mirrors 30, 31, 33 and 36, it is of course also possible to use any such elements which are suitable for influencing optical radiation in terms of its direction, for example, in particular, gratings, optical waveguides or the like.

Figure 4:
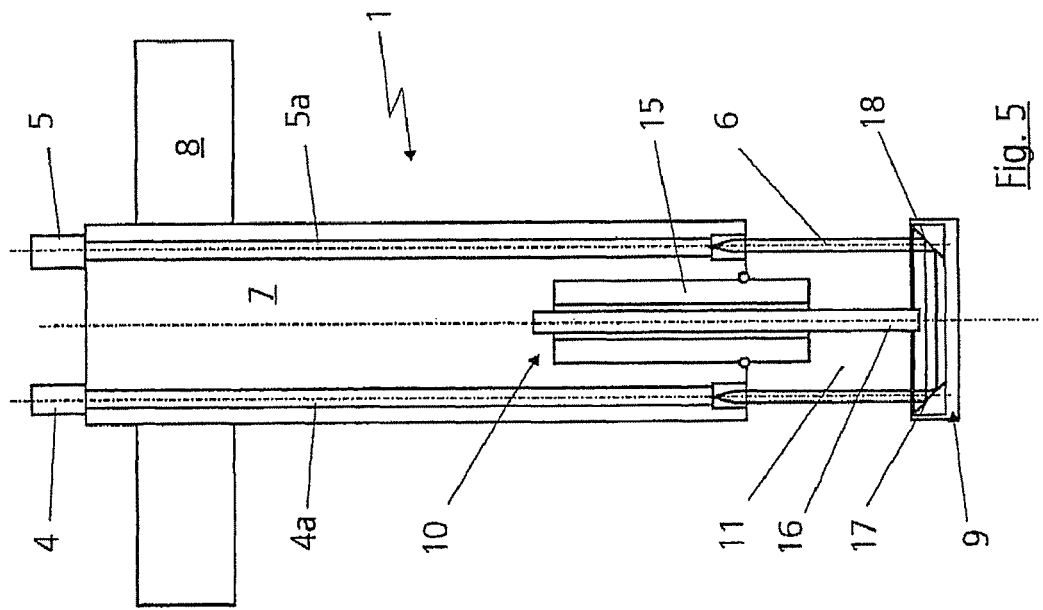
FIG. 4 shows the apparatus according to the invention with a more detailed illustration of the deflection device.

FIG. 4 shows a more detailed illustration of the apparatus 1. It shows that the adjustment device 10 has a guide or holding element 15 and a displacement element 16 which is mounted in the holding element 15 such that it can be displaced, and that the holding element 15 is connected to the housing 7 and the displacement element 16 to the deflection device 9. It is also possible, however, for the arrangement of these two components of the adjustment device 10 to be inverted. In the present case, the holding element 15 is in the form of a pipe in which the displacement element 16, which is in the form of a rod in the illustrated embodiment, is guided such that it can be displaced. However, other embodiments of the holding element 15 and of the displacement element 16 are, of course, also conceivable, for example in the form of threads or the like.

The adjustment device 10 can be operated, and thus the deflection device 9 can be adjusted, manually, in which case a graduation should be provided on the housing 7 which can be used to set and read off the layer thickness which is actually measured. Alternatively, the adjustment device 10 can also conceivably be actuated by electrical, hydraulic or pneumatic means, for which known devices can be used.

FIG. 4 furthermore shows that in the present case the deflection device 9 has two mirrors 17 and 18 which are used to deflect the optical radiation 6. Since this embodiment of the deflection device 9 is known per se, it needs no further explanation here. This is also true for the embodiment (not illustrated) in which the deflection device 9 is in the form of a prism.

Figure 5:
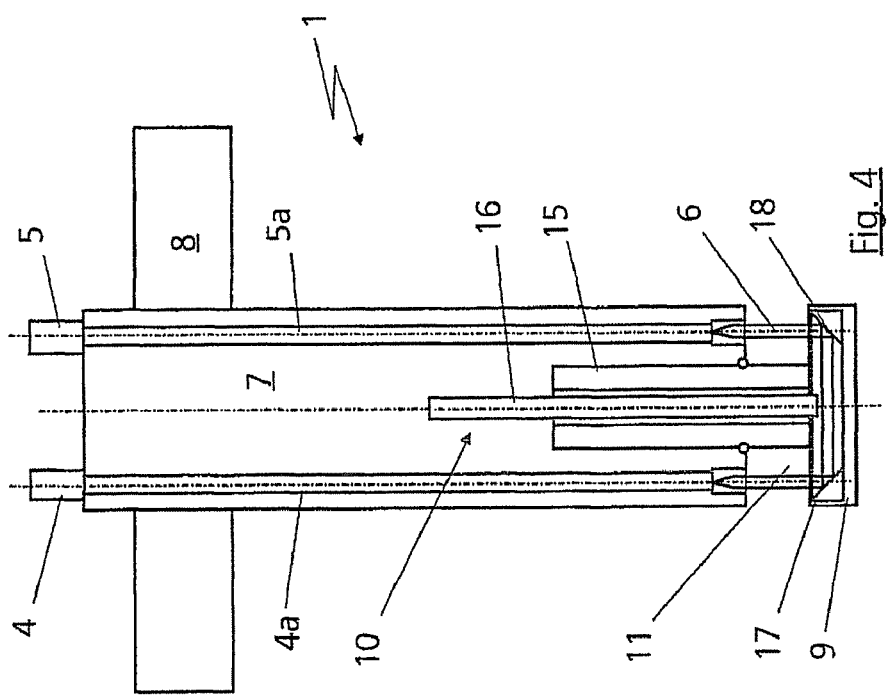
FIG. 5 shows the apparatus from FIG. 4 in another state of the adjustment device.

FIG. 5 illustrates the apparatus 1 in its extended state in which the distance between the deflection device 9 and the housing 7 has been increased by way of the adjustment device 10. Here, the layer thickness can be adjusted continuously or by way of the above-described graduation. It will be appreciated that an adjustment range of the deflection device 9 other than that illustrated in FIGS. 4 and 5 is also conceivable.

Figure 6:
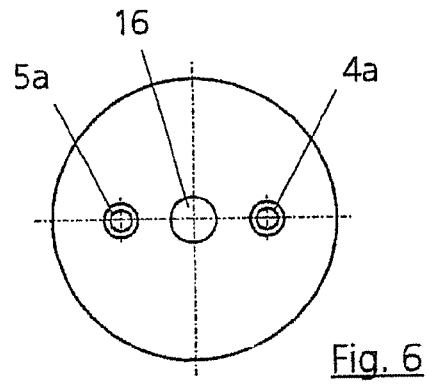
FIG. 6 shows a section along the line VI-VI from FIG. 4.

FIG. 6 shows a section through the apparatus 1 according to the line VI-VI from FIG. 4. It can be seen here that the holding element 15 of the adjustment device 10 is arranged substantially in the center of the housing 7. It will be appreciated that other arrangements of the displacement element 16 and thus of the holding element 15 are also possible. In this connection, the adjustment device 10 could also have more than the one holding element 15 and the associated displacement element 16, for example in order to increase stability. Furthermore, FIG. 6 illustrates the optical waveguide 4a of the transmitter 4 and the optical waveguide 5a of the receiver 5 in section. It will be appreciated that other arrangements thereof over the cross section of the housing 7 are conceivable in this case, too.

Figure 7:
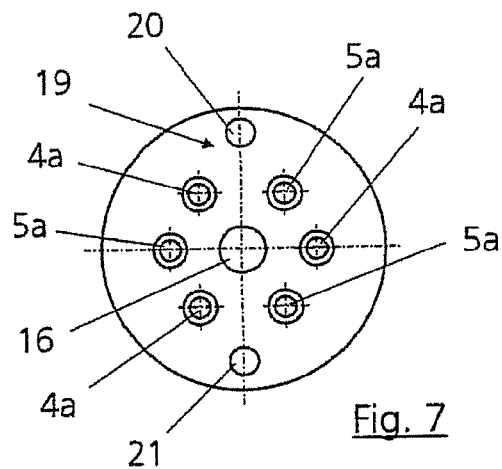
FIG. 7 shows a section similar to that of FIG. 6 in another embodiment of the apparatus and FIG. 8 shows a structural variant for realizing the adjustment device.

Another embodiment of the apparatus 1 is illustrated in the section shown in FIG. 7. Here, the adjustment device 10 is likewise arranged centrally inside the housing 7, but a larger number of transmitters 4 with corresponding optical waveguides 4a and receivers 5 with corresponding optical waveguides 5a is shown. A greater light throughput given the same wavelength is possible in this way or, if appropriate light sources are used, a combination of wavelength ranges with different optical waveguides, by means of which different measurements can be carried out by way of one measurement. Moreover, a photometer with two wavelengths can be illustrated in this manner.

FIG. 7 also illustrates a flushing device 19 which serves for flushing the hollow space 11 between the housing 7 and the deflection device 9 and has a supply line 20 for a cleaning agent and a suction line 21 for emptying the hollow space 11. The hollow space 11 can thus be flushed out without removing the apparatus 1 from the substance 2. As an alternative to the illustration shown in FIG. 7, both the supply line 20 and suction line 21 and the optical waveguides 4a and 5a, as well as the holding element 15 and the displacement element 16, can be located at different locations which are suitable for the respective intended use. As an alternative or in addition, to flushing the hollow space 11 using the supply line 20, it is also possible to introduce a reference medium into the hollow space 11 in order to be able to carry out specific comparative measurements. In addition, a drying device (not illustrated) for drying the hollow space 11, which has been flushed by way of the flushing device 19, can be provided, which drying device can be operated for example using compressed air or nitrogen and for which known devices can be used.

It is possible when measuring powders or other free-flowing substances to compress the substance 2 between the deflection device 9 and the housing 7 using the adjustment device 10 such that the substance 2 lies in a defined manner between the plane-parallel plates of the housing 7 and of the deflection device 9.

Figure 8:
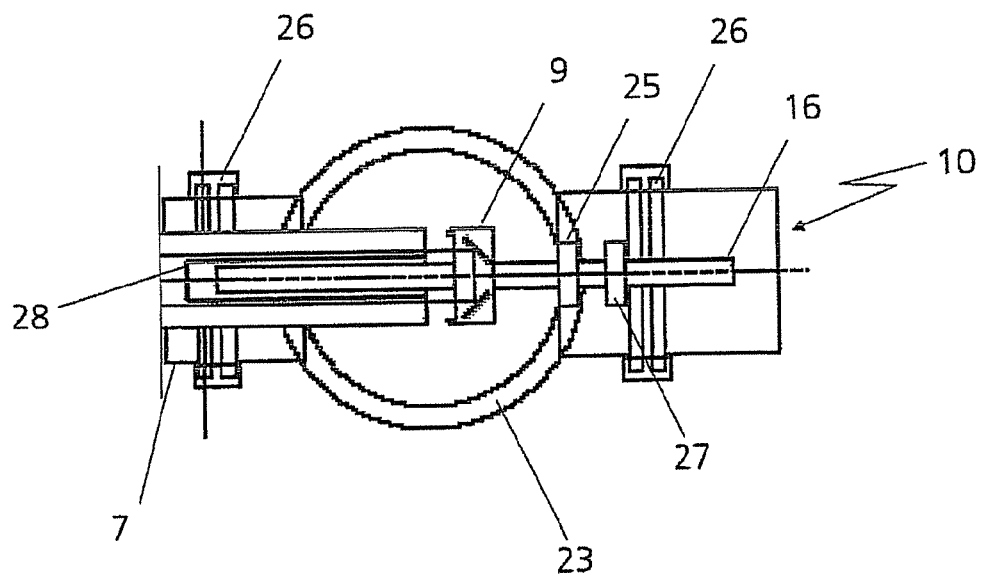

FIG. 8 shows a variant of the invention in which the substance to be measured is held in a pipe 23. As can be seen in FIG. 8, the housing 7 is inserted into the pipe 23 at a first end and the adjustment device 10 is inserted into the pipe 23 at a second end, which is opposite the first end, and fixed by corresponding retaining means 25. This means that the housing 7 and the adjustment device 10 are inserted into the pipe 23 in a manner such that the respective openings in the pipe 23 have a common central axis. The housing 7 and the housing of the adjustment device 10 can be fixed to the pipe 23 in each case by way of corresponding quick-release locks 26. This arrangement of the adjustment device 10 outside the housing 7 advantageously saves on installation space in the housing 7, and other components (not illustrated) can thus be accommodated in the housing 7 without difficulty. The adjustment device 10 comprises at least one actuating element 27 and one displacement element 16 which is mounted in the at least one actuating element 27 such that it can be displaced, with the actuating element 27 being fixed inside the adjustment device 10 and the displacement element 16 being connected to the deflection device 9. In the present case, the displacement element 16 is guided on both sides, i.e., for example, a guide element 28 which is in the form of a pipe and in which the displacement element 16, which is in the form of a rod, for example, is guided such that it can move in the longitudinal direction, is arranged in the housing 7, and the displacement element 16 is guided in the adjustment device 10 by way of the actuating element 27. It will be appreciated, however, that other embodiments of the guide element 28, of the actuating element 27 and of the displacement element 16 are also conceivable, for example in the form of threads or the like.

The adjustment device 10 can be operated and thus the deflection device 9 adjusted by way of the displacement element 16 manually. Alternatively, it is also conceivable to actuate the displacement element 16 by electrical, hydraulic or pneumatic means, for which purpose known actuating elements 27 can be used.

The invention claimed is:

1. An apparatus for measuring the concentration of a substance using optical radiation, said apparatus, comprising:
   a housing;
   at least one transmitter for emitting the optical radiation into a path, in use of the apparatus said path passing at least once through a layer of the substance, said layer having a thickness, said at least one transmitter being mounted on said housing or in said housing;
   at least one receiver for receiving at least a portion of the optical radiation which has passed at least once through the layer of the substance, said at least one receiver being mounted on said housing or in said housing;
   a deflection device disposed in said path between said transmitter and said receiver for deflecting the optical radiation toward said receiver, and
   an adjustment device for adjusting a distance between said deflection device and at least one of (i) said transmitter and (ii) said receiver, said distance being adjustable such that said thickness of the layer is adjusted by adjusting said distance and such that upon said distance being adjusted such that said deflection device is sufficiently close to said housing, a closed hollow space is formed between said housing and said deflection device.

2. An apparatus as claimed in claim 1, wherein said adjustment device includes at least one holding element and a displacement element, said displacement element being displaceably mounted in said at least one holding element device, one of said holding element and said displacement element being connected to said housing and the other one of said holding element and said displacement element being connected to said deflection device.

3. An apparatus as claimed in claim 1, wherein said adjustment device is manually adjustable.

4. An apparatus as claimed in claim 1, wherein said adjustment device is adjustable by electrical, hydraulic or pneumatic means.

5. An apparatus as claimed in claim 1, further comprising a seal arranged between said deflection device and said housing such that said closed hollow space is selectively sealed by said seal upon said distance being adjusted such that said deflection device is sufficiently close to said housing.

6. An apparatus as claimed in claim 1, further comprising a flushing device for flushing said hollow space between said housing and said deflection device.

7. An apparatus as claimed in claim 6, wherein said flushing device includes at least one supply line for a cleaning agent and further includes a suction line.

8. An apparatus as claimed in claim 6, further comprising a drying device for drying said hollow space between said housing and said deflection device.

9. An apparatus as claimed claim 1, further comprising a distance measuring device for measuring the distance between the deflection device and the at least one transmitter and the at least one receiver or a housing is provided.

10. An apparatus as claimed in claim 1, wherein the deflection device is arranged such that the optical radiation passes twice through the substance.

11. An apparatus as claimed in claim 1, wherein the deflection device is arranged such that the optical radiation passes only once through the substance.

12. An apparatus as claimed in claim 11, further comprising a pipe, through which the optical radiation is guided, is arranged in the region between the housing and the deflection device.

13. An apparatus as claimed in claim 1, wherein a plurality of transmitters and a plurality of receivers associated with the transmitters are provided.

14. An apparatus as claimed in claim 1, wherein the apparatus is configured such that the optical radiation which is incident on the substance to be measured and that component of the optical radiation which reaches the receiver are substantially at right angles with respect to one another.

15. An apparatus as claimed in claim 14, wherein the apparatus has a reflective element which is used to deflect that component of the optical radiation in the direction of the receiver which is emitted by the substance to be measured in the direction opposite the receiver.

16. An apparatus as claimed in claim 14, wherein the apparatus has means for the simultaneous or sequential measurement of absorption, fluorescence and scattering by the substance to be measured.

17. An apparatus as claimed in claim 1, wherein the substance is guided in a pipe having a first opening and a second opening, wherein said housing is inserted into said first opening of said pipe and adjustment device is inserted into said second opening of said pipe.

18. An apparatus as claimed in claim 17, wherein said housing and said adjustment device are inserted into said pipe in a manner such that said first opening and said second opening have a common central axis.

* * * * *